United States Patent [19]

Borretzen et al.

[11] Patent Number: 5,032,610

[45] Date of Patent: Jul. 16, 1991

[54] ACTIVITY AGAINST CARCINOMA AND METHOD FOR THE TREATMENT OF CARCINOMA

[75] Inventors: Bernt Borretzen; Rolf O. Larsen, both of Porsgrunn; John M. Dornish, Oslo; Reidar Oftebro, Hvalstad; Erick O. Pettersen, Oslo, all of Norway

[73] Assignee: Norsk Hydro AS, Oslo, Norway

[21] Appl. No.: 275,091

[22] Filed: Nov. 21, 1988

[51] Int. Cl.$^5$ .................... A61K 31/335; A61K 31/34
[52] U.S. Cl. ..................................... 514/467; 514/474
[58] Field of Search ............................... 514/474, 467

[56] References Cited

FOREIGN PATENT DOCUMENTS 148094 7/1985 European Pat. Off. ............ 514/467

0283139A2 9/1988 European Pat. Off. ............ 514/467

OTHER PUBLICATIONS

Cameron et al., Cancer Research 39, 663–681, Mar. 1979.

*Primary Examiner*—Jerome D. Goldberg
*Attorney, Agent, or Firm*—Wenderoth, Lind & Ponack

[57] ABSTRACT

The use of L-ascorbic acid, or a pharmaceutically acceptable salt thereof, in combination with 5,6-O-benzylidene-L-ascorbic acid, or 5,6-O-benzylidene-L-ascorbic acid deuterated at least at the 1-position of the aldehyde group of the benzylidene moiety, or a pharmaceutically acceptable salt of such acids, results in a synergistically enhanced cytotoxicity on human carcinoma cells.

17 Claims, No Drawings

ACTIVITY AGAINST CARCINOMA AND METHOD FOR THE TREATMENT OF CARCINOMA

BACKGROUND OF THE INVENTION

This invention relates to pharmaceutical compositions which have activity as anti-cancer agents against carcinoma and to methods for the treatment of carcinoma in patients.

It has been known for some time that the levels of ascorbic acid (vitamin C) are often low in cancer patients, which may be due to increased utilization of ascorbate by tumour cells. It has therefore been suggested that ascorbic acid might be a useful anti-cancer therapeutic agent in anti-cancer therapy. As reviewed by Cameron et al (Cancer Res., 39:663–681, 1979) some clinical trials have shown significant increases in survival times of cancer patients receiving ascorbate. However, to date, ascorbic acid has not found wide use as an anti-cancer agent.

More recently, it has been proposed to form adducts of ascorbic acid with other compounds in order to provide novel anti-cancer agents. Thus, for example, Elvin et al have reported (Eur. J. Cancer Clin. Oncol, 17(7), 1981, 759–65) that adducts of ascorbic acid with aldehydes such as methylglyoxal and acetylacrolein inhibit the growth of the Ehrlich ascites carcinoma in mice. Again, the use of ethers of, inter alia, ascorbic acid, and ketals and acetals thereof, as angiogenesis inhibiting agents is proposed in EP-A-0086544. Angiogenesis refers to the process of new blood vessel development, the proliferation of new blood vessels being involved in e.g. tumour growth.

More recently still, it has been disclosed in EP-A-0148094 that 5,6-O-benzylidene-L-ascorbic acid, and metal salts thereof, exhibit anti-cancer properties. This compound may be prepared by reacting L-ascorbic acid with either benzaldehyde in the presence of zinc chloride or with $\alpha,\alpha$-dimethoxytoluene, for example, and has the chemical structure shown below:

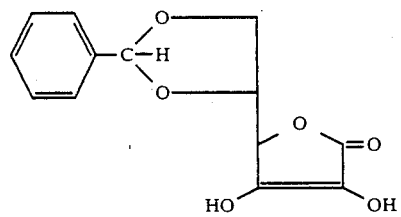

SUMMARY OF THE INVENTION

We have now unexpectedly discovered that the cytotoxic effects on human carcinoma cells of 5,6-O-benzylidene-L-ascorbic acid, and its metal salts, is synergistically enhanced if this anti-carcinoma agent is administered simultaneously with L-ascorbic acid, or a salt thereof. This ability of L-ascorbic acid to potentiate the anti-carcinoma effects of 5,6-O-benzylidene-L-ascorbic acid and its salts, opens up the possibility of new approaches to the treatment of carcinoma patients.

We have also discovered that at least a similar synergistic effect is exhibited with 5,6-O-benzylidene-L-ascorbic acid, deuterated at the 1-position of the aldehyde group of the benzylidene moiety, and pharmaceutically acceptable salts thereof.

Thus, in accordance with the present invention there is provided a pharmaceutical composition useful as an anti-cancer agent against carcinoma, comprising as active ingredients:

(i) L-ascorbic acid, or a pharmaceutically acceptable salt thereof; and (ii) a compound selected from 5,6-O-benzylidene-L-ascorbic acid, 5,6-O-benzylidene-L-ascorbic acid deuterated at the 1-position of the aldehyde group, and pharmaceutically acceptable salts of said acids.

The present invention encompasses the use of L-ascorbic acid, or a pharmaceutically acceptable salt thereof, for the manufacture of a medicament for use in an anti-carcinoma therapy which comprises the administration of a compound selected from 5,6-O-benzylidene-L-ascorbic acid, 5,6-O-benzylidene-L-ascorbic acid deuterated at the 1-position of the aldehyde group and pharmaceutically acceptable salts thereof.

Still further, the present invention provides a method for the treatment of carcinoma in a patient, which comprises administering to said patient:

(i) L-ascorbic acid or a pharmaceutically acceptable salt thereof; and (ii) a compound selected from 5,6-O-benzylidene-L-ascorbic acid, 5,6-O-benzylidene-L-ascorbic acid deuterated at the 1-position of the aldehyde group and pharmaceutically acceptable salts of said acids.

The deuterated 5,6-O-benzylidene-L-ascorbic acid useful herein may additionally be partially or completely deuterated at other positions of its molecular structure, i.e. in addition to the deuterium atom at the 1-position of the aldehyde group of the benzylidene moiety, one or more hydrogen atoms in the structure may be replaced by deuterium atoms.

DETAILED DESCRIPTION OF THE INVENTION

The deuterated compound employed in the present invention can have the formula

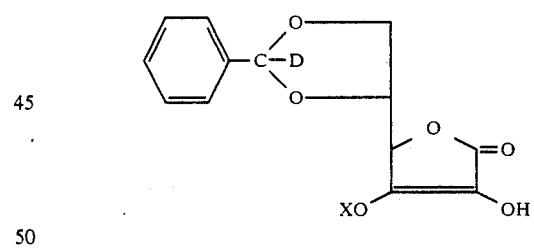

wherein X is hydrogen or a pharmaceutically acceptable metal cation.

The synergistic anti-carcinoma on which the present invention is predicated is demonstrated by the experiments described below. In these experiments we used L-ascorbic acid (abbreviated as "Asc") and either the sodium salt of 5,6-O-benzylidene-L-ascorbic acid (abbreviated as "BASS") or the sodium salt of 5,6-O-benzylidene-L-ascorbic acid deuterated at the 1-position of the aldehyde group of the benzylidene moiety (abbreviated as "BASS-$d_1$").

Biological materials and methods used to demonstrate the synergistic effect

Cell Culturing Techniques:

Human cells of the established line NHIK 3025, originating from a cervical carcinoma in situ (Nordbye, K., and Oftebro, R. Exp. Cell Res., 58:458, 1969), Oftebro, R., and Nordbye, K., Exp. Cell Res., 58:459-460, 1969) were cultivated in Medium E2a (Puck, T. T. et al., J. Exp. Med., 106:145-165, 1957) supplemented with 20% human and 10% horse serum (Grand Island Biological Co.). The cells are grown as monolayers in tissue culture flasks. The cells do not move around after they have attached, a quality which enables the same cells to be observed in an inverted microscope for several cell generations. The cells were kept in continuous exponential growth by frequent reculturing, i.e. every second and third day.

Cell Survival

For measurement of cell survival, appropriate numbers of cells were seeded in plastic Petri dishes ($\phi=5$ cm). The number of cells seeded into each dish was adjusted such that the number of surviving cells would be approximately 150 per dish. While exponentially growing (asynchronous) cells were trypsinized before seeding, synchronized cells were seeded immediately after selection. After about 2 hours, the cells had attached to the bottom of the dishes, and the treatment was started by replacing the medium with medium containing the appropriate drug concentration. After the desired time of treatment, the drug-containing medium was removed, and fresh medium was added. The dishes were rinsed once with the same medium as was to be added on addition or removal of drug. After 10 to 12 days at 37° C. in a $CO_2$ incubator, the cells were fixed in ethanol and stained with methylene blue before the colonies were counted.

Protein Synthesis:

The rate of protein synthesis was calculated as described in Rønning, Ø. W. et al., J. Cell Physiol., 107: 47-57, 1981. Briefly, cellular protein was labelled to saturation during a 2-day preincubation with ($^{14}C$)valine of constant specific radioactivity (0.5 Ci/mol) prior to the experiment. This was achieved by using a high concentration of valine so that the dilution of ($^{14}C$)valine by intracellular valine and by proteolytically generated valine will be negligible (Rønning, Ø. W., et al. Exp. Cell Res. 123:63-72, 1979), thus keeping the specific radioactivity at a constant level. The rate of protein synthesis was calculated from the incorporation of ($^3H$)valine of constant specific activity. The incorporation measurements were related to the total of ($^{14}C$) radioactivity in protein at the beginning of the respective measurement periods and expressed as the percentage per hour (Ronning, Ø. W. et al, J. Cell, Physiol. 107:47-57, 1981).

Biological effects

The cytotoxic effect of BASS and of ascorbic acid (Asc) used either alone or in simultaneous combination was measured on asynchronous, exponentially growing NHIK 3025 cells. The cells were treated for 24 hours at 37° C. while attached to the bottom of plastic Petri dishes and the number of cells able to form colonies after treatment was registered. In Table 1 the results of one single experiment are shown. The survival of cells treated with medium not containing any active ingredients. (i.e. 0 mM BASS and 0 mM Asc) was defined to be 1.0 and was used as the control.

TABLE 1

Surviving fraction of NHIK 3025 cells after 24 hours treatment with either BASS or Ascorbic acid (Asc) alone, or with BASS and Asc in simultaneous combination.

| Concentration of Asc (mM) | Concentration of BASS (mM) | | | |
|---|---|---|---|---|
| | 0 | 1.0 | 1.6 | 3.2 |
| 0 | 1.0 | 0.76 ± 0.02 | 0.52 ± 0.02 | 0.011 ± 0.001 |
| 0.8 | 0.91 ± 0.09 | 0.23 ± 0.02 | | |
| 1.2 | 0.80 ± 0.09 | 0.16 ± 0.02 | | |
| 1.6 | 0.61 ± 0.04 | | | |
| 2.4 | 0.40 ± 0.03 | 0.0045 ± 0.0009 | | |
| 3.2 | 0.11 ± 0.008 | 0.0018 ± 0.0003 | | |

The data in Table 1 show clearly that the use of BASS and Asc in combination induced a far stronger cytotoxic effect than either BASS or Asc alone. Using, for example, 1.0 mM BASS alone, the survival was 0.76. Similarly, for 1.2 mM Asc alone the survival was 0.8. Thus, if the two agents in combination induced only additional and mutually independent effects, then the survival would be expected to be $0.76 \times 0.8 = 0.61$. However, from Table 1, the survival after combined treatment with the two agents at the above concentrations was 0.16, i.e. the combined treatment resulted in an effect which was not merely additive, but rather synergistic, there being an almost four-fold increase in cytoxicity.

In a further experiment, similar to that reported in Table 1 above, the data summarized in Table 2 were obtained:

| Concentration of Asc (mM) | Concentration of BASS (mM) | | | | |
|---|---|---|---|---|---|
| | 0 | 0.5 | 1.0 | 1.6 | 3.2 |
| 0 | 1.0 | 0.91 ± 0.07 | 0.63 ± 0.08 | 0.44 ± 0.03 | 0.039 ± 0.004 |
| 0.8 | 0.95 ± 0.05 | | 0.30 ± 0.02 | 0.12 ± 0.01 | |
| 1.2 | 0.69 ± 0.02 | 0.48 ± 0.03 | 0.19 ± 0.01 | 0.049 ± 0.002 | |
| 1.6 | 0.54 ± 0.02 | 0.29 ± 0.01 | 0.096 ± 0.003 | 0.026 ± 0.002 | |
| 2.4 | 0.29 ± 0.01 | 0.070 ± 0.004 | 0.016 ± 0.001 | | |
| 3.2 | 0.087 ± 0.010 | | | | |

From Table 2, the same synergistic effect of the present invention can again be seen. Even for shorter treatment times, for example 4 hours, the same synergism is demonstrated, as can be seen from Table 3 below:

TABLE 3

Surviving fraction of NHIK 3025 cells after 4 hours treatment with either BASS or Asc alone, or with the two active ingredients in simultaneous combination.

| Concentration of Asc (mM) | Concentration of BASS (mM) | | |
|---|---|---|---|
| | 0 | 1.6 | 3.2 |
| 0 | 1.0 | 0.80 ± 0.05 | 0.36 ± 0.03 |
| 1.6 | 0.91 ± 0.01 | 0.079 ± 0.03 | |
| 3.2 | 0.27 ± 0.03 | | |

In our British Patent Application No. 8705780 (corresponding to now published European Patent Application No. 0283139) we have taught that certain aromatic aldehydes and derivatives thereof have an enhanced anti-cancer activity in vivo when the compounds are deuterated at the 1-position of the aldehyde group. We have therefore conducted an experiment to test the cytotoxic effect of deuterated BASS (BASS-$d_1$) when it is used in conjunction with ascorbic acid. The results are presented in Table 4 below:

TABLE 4

Surviving fraction of NHIK 3025 cells after 24 hours treatment with 1 mM of either BASS or BASS-$d_1$ alone or in simultaneous combination with various concentrations of Asc.

| | Concentration of Asc (mM) | | | |
|---|---|---|---|---|
| | 0 | 0.8 | 1.2 | 2.4 |
| BASS (1.0 mM) | 0.62 ± 0.05 | 0.23 ± 0.02 | 0.10 ± 0.01 | 0.0072 ± 0.0008 |
| BASS-$d_1$ (1.0 mM) | 0.55 ± 0.05 | 0.20 ± 0.01 | 0.097 ± 0.014 | 0.0029 ± 0.0003 |

From Table 4 it will be seen that the synergistic effect is demonstrated at a nearly equivalent level whether BASS or BASS-$d_1$ is used, although BASS-$d_1$ appears to be somewhat superior at least at higher concentrations.

In order to determine if the synergistic effect is obtained with other sugars, we have treated NHIK 3025 cells for 24 hours with BASS in combination with glucose. The results of such an experiment are shown in Table 5 below where cell survival is registered after treatment with 1.6 mM BASS in combination with various concentrations of glucose added to the cell culture medium.

TABLE 5

Surviving fraction of NHIK 3025 cells after 24 hours treatment with 1.6 mM BASS in simultaneous combination with varying concentrations of glucose.

| | Concentration of glucose in medium (mM) | | | | |
|---|---|---|---|---|---|
| | 0 | 1 | 2 | 4 | 8 |
| BASS (1.6 mM) | 0.24 ± 0.03 | 0.25 ± 0.02 | 0.18 ± 0.02 | 0.20 ± 0.01 | 0.19 ± 0.02 |

From Table 5 it can be seen that glucose does not improve the cell-inactivating ability of BASS in any manner, there being no statistically significant improvement in the cytotoxicity of the BASS between the absence of glucose and the presence of glucose even up to 8 mM.

We have also studied the effect of L-ascorbic acid used in combination with other aromatic aldehydes or derivatives of aldehydes, such as 4,6-O-benzylidene glucose, but again without observing any synergistic effects.

From earlier studies, it is known that determination of protein synthesis inhibition is a useful measure of anti-cancer activity. In the present study we have tested the protein synthesis inhibition as induced by both BASS and Asc alone, and by the two active agents in simultaneous combination. The experiment also included samples treated similarly, but where BASS-$d_1$ was used instead of BASS. The results are presented in Table 6 below:

TABLE 6

Protein Synthesis, given as percent of total cellular protein per hour, of NHIK 3025 cells after treatment with either BASS, Bass-$d_1$, or Asc alone, or with BASS or BASS-$d_1$ in simultaneous combination with Asc. Protein synthesis was registered during the first hour after addition of active agents.

| | Concentration of BASS or BASS-$d_1$ (mM) | | | |
|---|---|---|---|---|
| Concentration of Asc (mM) | 0 | BASS 1.0 | Bass-$d_1$ 1.0 | BASS 3.2 | BASS-$d_1$ 3.2 |
| 0 | 4.5 ± 0.1 | 3.06 ± 0.02 | 3.03 ± 0.16 | 1.71 ± 0.05 | 2.00 ± 0.03 |
| 0.1 | | 2.90 ± 0.05 | 2.76 ± 0.07 | | |
| 0.3 | | 2.5 ± 0.1 | 2.55 ± 0.08 | | |
| 0.6 | | 2.4 ± 0.1 | 2.07 ± 0.05 | | |
| 1.0 | 2.96 ± 0.04 | 1.73 ± 0.07 | 1.66 ± 0.01 | | |
| 3.2 | 1.5 ± 0.2 | | | | |

From the results presented in Table 6, it is seen that the rate of protein synthesis is 4.5%/h (meaning per cent of the total cellular protein per hour) in the control. Using 3.2 mM of either BASS or Asc alone resulted in a reduction in the rate of protein synthesis to 1.5–1.7 %/h. However, when both drugs are used simultaneously a concentration of 1.0 mM BASS and 1.0 mM Asc is enough to reduce the rate of protein synthesis to this level (1.73 %/H).

From the data given in Tables 1–6 above, it is clear that the compounds BASS or BASS-$d_1$, on the one hand, and Asc on the other do not act independently when used together. Furthermore, the synergistic effect of Asc and BASS or BASS-$d_1$ is stronger than the effect of one of the drugs alone at a concentration similar to the sum of concentrations used in the combination. This is an indication that the synergistic effect induced by the two drugs BASS and Asc must result from either a reaction product between the two, or a cellular sensitization of some kind. This sensitization could be a result of increased cellular uptake, inhibition of repair processes, or simply reduced chemical restitution. However, at the present time, the explanation for the synergistic effects which we have observed are not known.

Although the above experiments utilized the sodium salts of 5,6-O-benzylidene-L-ascorbic acid and the partially deuterated derivative thereof, it is within the scope of the present invention to use other pharmaceutically acceptable salts, in particular other pharmaceutically acceptable alkali and alkaline earth metal salts. The sodium salts are, however, preferred, being well-soluble in water.

Likewise, in some instances it may be preferred to use a pharmaceutically acceptable salt of L-ascorbic acid rather than the free acid itself.

Pharmaceutical compositions containing the active ingredients of the present invention may be formulated in numerous ways well known to those skilled in the art, with pharmaceutically acceptable excipients or carriers. Such pharmaceutical compositions according to this invention may be administered orally or parenterally. For oral administration, the compositions can be presented in the form of tablets, capsules, granules or powders. For parenteral administration, the compositions may be presented in a form suitable for injection or intravenous infusion or as a suppository.

The active ingredients of the compositions may be formulated by being incorporated with conventional pharmaceutically acceptable carriers, either solid or liquid. Surfactants, vehicles, lubricants, adjuvants and pharmacologically acceptable film-forming materials, for example, may be used as is known in the pharmaceutical formulation art.

The content of the active ingredients in the pharmaceutical compositions according to this invention may vary, depending on the form of the formulation. For oral administration, the content of 5,6-O-benzylidene-L-ascorbic acid or pharmaceutically acceptable salt thereof, will usually be about 0.1 to 20% by weight, with an equivalent amount of ascorbic acid or salt thereof then being present in the composition. For absorption through mucous membranes, the amount of each active ingredient would be about 0.1 to 10% by weight at a preferred ratio of 1:1 for parenteral administration. Corresponding amounts will apply for the deuterated compounds.

Although it is preferred that the two active ingredients should be formulated together in a pharmaceutical composition to ensure that the patient receives the desired dosage of each active ingredient for optimum therapeutic effect, nonetheless it is within the scope of this invention to administer each active ingredient separately, provided that the patient receives the correct dosage of each active ingredient to ensure that the synergistic effect is manifested in the patient.

Suitable ranges for the dosage of each of the active ingredients are as follows. For oral administration 5,6-O-benzylidene-L-ascorbic acid or salt thereof, or of a deuterated aldehyde derivative, will be used in the range of 10–75 mg per kg body weight up to twice daily. Acceptable ranges for ascorbic acid, or salt thereof, will be from 10–100 mg per kg body weight up to twice daily. For intravenous infusion or injection suitable ranges for 5,6-O-benzylidene-L-ascorbic acid or alkaline earth salts thereof, or of the deuterated compound will be 10–75 mg per kg body weight up to twice daily. Ascorbic acid as sodium ascorbate or buffered with sodium carbonate will be present in the drug combination at physiologically acceptable levels, normally approximately 10–100 mg per kg body weight up to twice daily.

Thus, for an adult patient, 1.5–3 g of BASS or BASS-$d_1$ in combination with up to 5 g L-ascorbic acid, or salt thereof, will preferably be given orally per day. For infusion, an adult patient preferably would receive 1.5–3 g of BASS or BASS-$d_1$, either in combination with 5–10 g of L-ascorbic acid or salt thereof or singly, in the latter case the L-ascorbic acid or salt thereof then also being given singly.

Physiological pH of injectables or infusion drug combinations will be established by inclusion of buffering agents as is known in the pharmaceutical art.

We claim:

1. A pharmaceutical composition as an anti-cancer agent against carcinoma, comprising as active ingredients:

(i) a therapeutically effective amount, for the treatment of carcinoma, of L-ascorbic acid or a pharmaceutically acceptable salt thereof; and (ii) a therapeutically effective amount, for the treatment of carcinoma, of a compound selected from the group consisting of 5,6-O-benzylidene-L-ascorbic acid deuterated in the benzylidene moiety at least at the 1-position of the aldehyde group of the benzylidene moiety, and pharmaceutically acceptable salts of said acids.

2. A pharmaceutical composition according to claim 1, wherein said pharmaceutically acceptable salts are selected from the group consisting of alkali metal salts and alkaline earth metal salts.

3. A pharmaceutical composition according to claim 1 or 2, wherein said active ingredient (ii) is the compound of the formula:

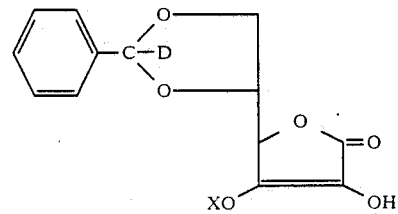

wherein X is hydrogen or a pharmaceutically acceptable metal cation.

4. A pharmaceutical composition according to claim 3, further comprising a pharmaceutically acceptable carrier or excipient for oral administration.

5. A pharmaceutical composition according to claim 1 or 2, further comprising a pharmaceutically acceptable carrier or excipient for oral administration.

6. A pharmaceutical composition according to claim 5, comprising from 0.1 to 20% by weight of said active ingredient (ii) and an equivalent amount of said active ingredient (i).

7. A pharmaceutical composition according to claim 1 or 2, further comprising a pharmaceutically acceptable carrier or excipient for parenteral administration.

8. A pharmaceutical composition according to claim 3, further comprising a pharmaceutically acceptable carrier or excipient for parenteral administration.

9. A pharmaceutical composition according to claim 7, comprising from 0.1 to 10% by weight of each of said active ingredients (i) and (ii).

10. A pharmaceutical composition according to claim 1, wherein said active ingredient (ii) is 5,6-O-benzylidene-L-ascorbic acid deuterated in the benzylidene moiety at least at the 1-position of the aldehyde group of the benzylidene moiety.

11. A method for the treatment of carcinoma in a patient, which comprises administering to said patient:
(i) a therapeutically effective amount, for the treatment of carcinoma, of L-ascorbic acid or a pharmaceutically acceptable salt thereof; and
(ii) a therapeutically effective amount, for the treatment of carcinoma, of a compound selected from the group consisting of 5,6-O-benzylidene-L-ascorbic acid deuterated in the benzylidene moiety at least at the 1-position of the aldehyde group of the benzylidene moiety, and pharmaceutically acceptable salts of said acids.

12. A method according to claim 11, wherein said active ingredients (i) and (ii) are administered simultaneously by the administration of a composition comprising said active ingredients (i) and (ii).

13. A method according to claim 11, wherein said active ingredients (i) and (ii) are separately administered.

14. A method according to any one of claims 11, 12 and 13, wherein said active ingredient (ii) is the compound of the formula:

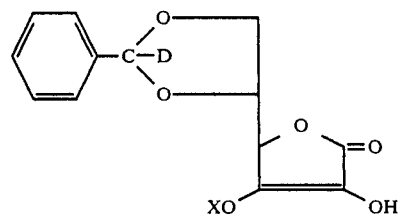

wherein X is hydrogen or a pharmaceutically acceptable metal cation.

15. A method according to any one of claims 11, 12 and 13, wherein from 1.5-3 g of said active ingredient (ii) are administered orally to an adult patient per day in conjunction with up to 5 g of said active ingredient (i).

16. A method according to any one of claims 11, 12 and 13, wherein from 1.5-3 g of said active ingredient (ii) are administered by infusion to an adult patient per day in conjunction with from 5-10 g of said active ingredient (i).

17. A method according to claim 11, wherein said (ii) is 5,6-O-benzylidene-L-ascorbic acid deuterated in the benzylidene moiety at least at the 1-position of the aldehyde group of the benzylidene moiety.

* * * * *